United States Patent [19]

Lin

[11] Patent Number: 4,849,543

[45] Date of Patent: Jul. 18, 1989

[54] PROCESS FOR THE HYDROFORMYLATION/MICHAEL ADDITION OF ACRYLATES TO DIESTERS

[75] Inventor: Jiang-Jen Lin, Round Rock, Tex.

[73] Assignee: Texaco Inc., White Plains, N.Y.

[21] Appl. No.: 798,543

[22] Filed: Nov. 15, 1985

[51] Int. Cl.$^4$ .............................................. C07C 69/66
[52] U.S. Cl. .................................. 560/177; 560/175
[58] Field of Search ................................. 560/175, 177

[56] References Cited

FOREIGN PATENT DOCUMENTS 39-3020  3/1964  Japan ..................................... 560/177
73822    6/1977  Japan ..................................... 560/175

Primary Examiner—Werren B. Lone
Attorney, Agent, or Firm—Jack H. Park; Kenneth R. Priem; Cynthia L. Kendrick

[57] ABSTRACT

This invention concerns a process for the production of diesters by hydroformylation/Michael addition of alkyl acrylates, which comprises contacting the alkyl acrylate with carbon monoxide and hydrogen in the presence of a catalyst system comprising a rhodium-containing compound, excess phosphine-containing ligand, a nitrogen-containing compound and a solvent at a temperature of 70°–150° C. and a pressure of 500–4000 psi.

7 Claims, No Drawings

PROCESS FOR THE HYDROFORMYLATION/MICHAEL ADDITION OF ACRYLATES TO DIESTERS

This invention relates to a process for the preparation of diesters from alkyl acrylates and synthesis gas in the presence of a rhodium hydroformylation catalyst, a phosphine-containing ligand and a nitrogen-containing compound.

More specifically, this invention concerns the hydroformylation of methyl acrylate and ethyl acrylate to dimethyl 2-formyl-2-methylglutarate and diethyl 2-formyl-2-methylglutarate, respectively, by hydroformylation and Michael addition in one step using a rhodium catalyst under relatively mild reaction conditions.

This novel synthesis involves two reactions occurring in one vessel and affords a C-7 diester product directly. The first step is the hydroformylation of acrylate at the α-position, followed by a second reaction which is Michael addition of the acrylate intermediate to another molecule of acrylate. The process required the presence of an amide and excess triphenylphosphine to facilitate the Michael addition and hydroformylation reactions respectively.

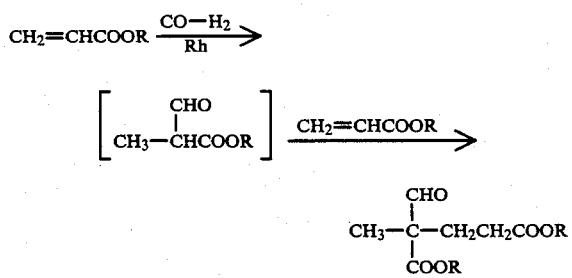

BACKGROUND OF THE INVENTION

The compound dimethyl 2-formyl-2-methylglutarate is an important intermediate for producing amines or diols or triols. Whether the former or latter is produced depends whether the intermediate dimethyl 2-formyl-2-methylglutarate is subsequently subjected to reductive amination or reduction, respectively. The diesters, amines and diols or triols are important in polymer applications, such as polyesters. However, nothing in the prior art teaches or suggests a convenient method for synthesizing these intermediate compounds. Nowhere is there described a catalyst system such as in the instant process for producing these intermediates from acrylates and synthesis gas by a novel reaction.

Murata et al. have reported on the relative activity of various complexes formed in situ from dicobalt octacarbonyl and various di(tertiary phosphines) as ligands for the hydroformylation of methyl acrylate. The complexes are more active than $Co_2(CO)_8$ alone and the most active of the catalyst complexes was active even at low pressures where decomposition of $Co_2(CO)_8$ occurs. See Bull. Chem. Soc. Jpn. 53, 214–218 (1980).

A study reported by Jardine in Polyhedron, No. 7–8, 569–605, 1982 provides further insight into a comparison of carbonylhydrido tris(triphenylphosphine)rhodium(I) $RhH(CO)(PPh_3)_3$ as a hydroformylation catalyst and concludes that though $RhH(CO)(PPh_3)_3$ is the best hydroformylation catalyst, that it is disappointing in other reactions, that chlorotris(triphenylphosphine)rhodium(I) is probably a more generally useful hydrogenation catalyst and dichloro tris(triphenylphosphine)ruthenium(II) is probably a more effective isotope exchange catalyst.

In J. Mol. Cat. 16 (1982) 195–207, Mitsuo et al. describe experiments wherein phosphine complexes are used in conjunction with rhodium-catalyzed low pressure hydroformylation of typical terminal olefins at pressures substantially lower than will normally work.

In J. Falbe, "New Syntheses With Carbon Monoxide", Springer-Verlag, Berlin Heidelberg New York 1980, Chapter 1 discusses the hydroformylation of methyl acrylate by using rhodium and cobalt catalysts (page 119 and 120). Under similar reaction conditions, a cobalt catalyst is used to hydroformylate methyl acrylate to produce methyl β-formylpropionate as the predominant product. In contrast, rhodium produced α-formylpropionate as the major product. Furthermore, the selectivity was affected by the addition of triphenylphosphine.

Generally in the prior art what is taught or suggested is the rhodium catalyzed hydroformylation of, for example, olefins. Nothing in the art teaches the novel reaction of the instant invention wherein diesters are formed via the hydroformylation/Michael addition of alkyl acrylates. This appears to be a new reaction. It would be desirable to invent a process for such a reaction, especially if the conversion and selectivity for the desired diesters were high. These diesters can be used as intermediates for producing amines, diols and triols.

SUMMARY OF THE INVENTION

In accordance with the present invention methyl acrylate and synthesis gas undergo hydroformylation and Michael addition in the presence of a rhodium-containing compound, acetamide, a phosphine-containing ligand and optionally a solvent at a temperature of 70°–150° C. and a pressure of 500–4000 psi. In another embodiment ethyl acrylate and synthesis gas undergo hydroformylation in the presence of a rhodium-containing compound and Michael addition in the presence of an amide such as acetamide, benzamide and N-methylpyrrolidone, DMF, or a tertiary amine such as tri-n-propylamine. There is good conversion of acrylates and the diesters are produced with good conversion and selectivity and are useful as intermediates for di- and tricarboxylic acid, amines and for diols and triols, for polymer applications, such as polyesters.

DETAILED DESCRIPTION OF THE PREFERRED INVENTION

In the narrower and more preferred practice of this invention diesters are prepared from alkyl acrylates and synthesis gas by a process which comprises contacting said acrylates and synthesis gas with a catalyst system comprising a rhodium-containing compound, an excess of phosphine ligand, a amide compound and a solvent at a temperature of at least 50° C. and a pressure of at least 500 psi until there is substantial formation of the desired diesters.

The general reaction can be represented by:

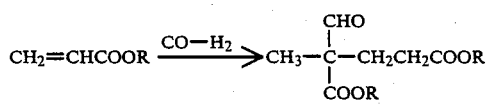

Recovery of the diesters and by-products from the reaction product can be carried out in any convenient or conventional manner such as by distillation, extraction etc.

In general, the components of the hydroformylation reaction mixture, including the alkyl acrylate compound, hydroformylation catalyst, phosphine-containing ligand and solvent may be added in any sequence as long as good agitation is employed to provide a good dispersion or a homogeneous reaction mixture. For example, the following represent some variations insofar asthe addition of catalyst components, solvent and alkyl acrylate addition that can be made without departing from the inventive process. These modifications include:

1. The catalyst may be preformed and added to the solvent prior to addition of the alkyl acrylate and other reactants.

2. Preferably, to minimize stability problems with the catalyst, the catalyst is best formed in situ, usually by mixing the solvent and acrylate followed by the addition of the rhodium-containing compound, phosphine ligand and nitrogen-containing compound to form the reaction mixture.

3. After using either variation 1 or 2 the catalyst containing reaction mixture is pressurized with CO and hydrogen and heated until the product is formed.

The reactants used in the process of the invention comprise alkyl acrylates. Suitable acrylates comprise alkyl acrylates wherein the alkyl group contains 1 to 10 carbon atoms. Typical compounds include methyl, ethyl, n-propyl, n-butyl and n-octyl acrylate. The preferred reactant for the embodiment by which dimethyl 2-formyl-2-methylglutarate is produced is methyl acrylate. The preferred reactant for the embodiment by which diethyl 2-formyl-2-methylglutarate is produced is ethyl acrylate.

The rhodium-containing compound to be used in the catalyst in practice of this invention may be chosen from a wide variety of organic or inorganic compounds, complexes, etc. as will be shown and illustrated below. It is only necessary that the catalyst precursor actually employed contain said rhodium in any of its ionic states. The actual catalytically active species is then believed to comprise rhodium in complex combination with one or more phosphine promoters, a nitrogen-containing compound and a solvent.

The rhodium compound can be selected from the group consisting of rhodium oxides, salts of inorganic acids, such as rhodium chloride, bromide, iodide, sulfide and salts of aliphatic monocarboxylic acids such as rhodium acetate, propionate, oxylate and malonate.

Other suitable inorganic or organic salt-like compounds falling within the scope of the invention are salts of heteropolyacids containing rhodium, such as the salts of alkalai metals or alkaline earth metals, ammonium salts or amine salts. By way of specific examples there may be mentioned as oxides: $Rh_2O$, $Rh_2O_3$, $RhO_2$ and $RhO_3$.

Salts of inorganic acids include rhodium chloride $RhCl_3$, rhodium bromide $RhBr_3$, rhodium iodide $RhI_3$, and rhodium sulfide $Rh_2S_3$. Salts of carboxylic acids include rhodium acetate $[Rh(CH_3CO_2)_3]$ and rhodium oxylate $[Rh_2(C_2O_4)_3]$.

Other derivatives which can be employed to carry out the process of the invention include the carbonyl derivatives of rhodium such as rhodium tricarbonyl $[Rh(CO)_3]$, rhodium tetracarbonyl $[Rh(CO)_4]_2$, the compound $Rh_4(CO)_{17}$ and the halogencarbonyl derivatives of rhodium such as rhodium dicarbonyl chloride $[Rh(CO)_2Cl]_2$, rhodium dicarbonyl bromide $[Rh(CO)_2]Br$ and rhodium dicarbonyl iodide $[Rh(CO)_2]I$.

The preferred catalyst is a rhodium carbonyl containing a large excess of tertiary phosphine such as triphenylphosphine. The best example is hydridorhodium tris(triphenylphosphine)rhodium.

In the first embodiment of the process of this invention methyl acrylate is reacted with carbon monoxide and hydrogen in the presence of a hydroformylation catalyst comprising $HRh(CO)(PPh_3)_3$, excess triphenylphosphine and acetamide to form dimethyl 2-formyl-2-methylglutarate. The reaction can be represented by the equation:

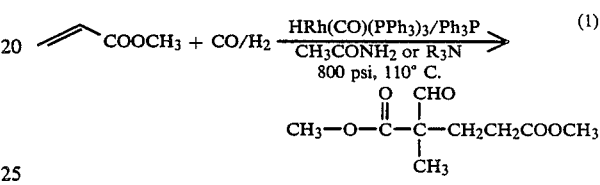

(1)

The reaction allows up to 65% conversion of methyl acrylate and up to 70% selectivity for the desired product. In order to obtain these desired results an excess of triphenylphosphine ligand appears to be essential.

Also, in order to obtain Michael addition at the α-position of methyl acrylate, the presence of a nitrogen-containing compound is needed in addition to the triphenylphosphine. Suitable nitrogen-containing compounds are selected from compounds represented by the formulas $RCONH_2$, $RCONR'_2$ or $R_3N$, where R represents an alkyl group containing 1 to 10 carbon atoms or an aryl radical. In $RCONR'_2$, R and R' can be a hydrogen or an alkyl radical with 1 to 10 carbons. Suitable compounds include DMF, N,N-dimethylacetamide, N-methyl pyrrolidone, etc. Suitable nitrogen-containing compounds include acetamide, benzamide, propionamide and tripropylamine. Preferred compounds include tripropylamine and acetamide. In the first step of the invention good results were obtained with acetamide.

In the second step of the invention the rhodium hydroformylation of diethyl acrylate afforded the Michael addition product, diethyl 2-formyl-2-methylglutarate, at yields as high as 66%.

In order to produce the Michael addition product, diethyl 2-formyl-2-methylglutarate, a suitable amide is required in addition to triphenylphosphine. Amides which will bring about the desired results are selected from the group consisting of secondary amides including, but not limited to N,N-dimethylacetamide and dimethylformamide.

It is noted that when secondary amines are used as the solvent (in the second embodiment) the effect is to lower the conversion and selectivity to the desired diester product. For instance, in the presence of a secondary amine the following product distribution was observed:

-continued (I) 31% + Et$_2$NCH$_2$CH$_2$COOC$_2$H$_5$ (IV) 48%

The temperature range which can be employed for hydroformylation is a variable which is dependent upon experimental factors including the particular acrylate compound employed, the total pressure, the mole ratio of hydrogen and carbon monoxide used, the concentrations of reactants and catalyst, and particularly the choice of rhodium catalyst and solvent among other things. Using methyl acrylate or ethyl acrylate as the substrate and HRh(CO)(PPh$_3$)$_3$ as a representative catalyst, an operable range is from about 70° C. to 150° C. or more when superatmospheric pressures of greater than 100 psig are employed. A narrower range of 80° C. to 120° C. represents the preferred temperature range when the aforementioned acrylates are hydroformylated.

The pressure range which can be employed for hydroformylation is a variable which is also dependent on the factors mentioned above. Using HRh(CO)(PPh$_3$)$_3$/Ph$_3$P along with CH$_3$CONH$_2$ as a representative catalyst and solvent, and methyl or ethyl acrylate as the substrate, an operable pressure range is from about 500 to 4000 psig, or more with the mole ratio of H$_2$:CO being 1:1 when a temperature range of from about 25° to 125° C. is employed. A narrower range of from 500 to 2000 psig represents the preferred pressure range when the narrower temperature range of 80° C. to 120° C. is employed The H$_2$:CO mole ratio may be varied over a range of from 30:1 to 1:30 when suitable temperatures and pressures are employed. A preferred narrower range is from 2:1 to 1:2 of hydrogen:carbon monoxide.

As previously indicated in the analogous discussion on temperatures and pressures required in the reaction, experimental variables are important in arriving at reaction times. Generally, substantial conversions (up to 70%) of the methyl acrylate to dimethyl-2-formyl-2-methylglutarate can almost always be accomplished within 18 hours, with 2 to 4 hours representing the more usual reaction time interval.

In the process of this invention the molar ratio of rhodium-containing compound to the triphosphine ligand is significant. The experimental work performed indicates that an excess of ligand of about at least 3 moles of triphenylphosphine for each mole of rhodium-compound complex is required for good selectivity. Preferably a ratio of from 10 to 500 moles of triphenylphosphine for each mole of rhodium-containing compound has been established to yield the optimum amount of glutarate product. Most preferred is ca. 50 moles per mole of rhodium compound. This preferred ratio is based upon the hydroformylation of methyl or ethyl acrylate.

Experimental work indicates that an initial molar ratio of 50 moles to 5000 moles of acrylates per mole of rhodium catalyst can be employed in most instances. The minimal ratio would be about 0.0001 moles of catalyst per mole of acrylate.

The novel hydroformylation is run most conveniently in the presence of a solvent. The solvent useful in the process of this invention is an oxygenated hydrocarbon, i.e., a compound composed only of carbon, hydrogen and oxygen and one in which the only oxygen atoms present are in ether groups, ester groups, ketone carbonyl groups or hydroxyl groups of alcohols. Generally, the oxygenated hydrocarbon will contain 3 to 12 carbon atoms and preferably a maximum of 3 oxygen atoms. The solvent must be substantially inert under reaction conditions.

Preferred ester type solvents are the aliphatic and acrylic carboxylic acid monoesters as exemplified by butyl acetate, methyl benzoate, isopropyl iso-butyrate, and propyl propionate as well as dimethyl adipate. Useful alcohol-type solvents include monohydric alcohols such as cyclohexanol, 1-hexanol, 2-hexanol, neopentanol, 2-octanol, etc. Suitable ketone-type solvents include, for example, cyclic ketones such as cyclohexanone, 2-methylcyclohexanone, as well as acyclic ketones such as 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, etc., alkanols such as methanol and acid esters such as methyl acetate.

The most preferred solvents and those which seem to most noticeably effect an increase in selectivity to diesters include p-dioxane or methyl isobutyl ketone.

Acrylate hydroformylation and Michael addition products, including dimethyl 2-formyl-2-methylglutarate and diethyl 2-formyl-2-methyl glutarate may be isolated by the usual chemical or physical techniques, such as distillation, solvent extraction, chromatography, etc. Identification is by nuclear magnetic resonance. Unless otherwise specified all percentages are by weight and all temperatures are in centigrade rather than fahrenheit.

Conversion as defined herein represents the extent of conversion of the reacting alkyl acrylate to other products. Conversion is expressed as a percentile and is calculated by dividing the amount of alkyl acrylate consumed during hydroformylation by the amount of acrylate originally charged and multiplying the quotient by 100.

Yield, as defined herein, represents the efficiency in catalyzing the desired hydroformylation reaction relative to other undesired reactions. In this instance hydroformylation and Michael addition to diesters is the desired conversion. Yield is expressed as a percentile, and is calculated by determining the amount of, for example dimethyl 2-formyl-2-methylglutarate or 2-methyl-2-formylglutarate product formed, divided by the amount of acrylate charged and multiplying the quotient obtained by 100.

Selectivity, as defined herein, is the efficiency in catalyzing a desired reaction relative to the other undesired conversion. Selectivity is expressed as a percentile, and is calculated by determining the amount of diester product formed, divided by the total amount of products formed, and multiplying the quotient obtained by 100.

Having described the inventive process in general terms, the following examples are submitted to supply specific and illustrative embodiments.

EXAMPLE I

A 300 ml stirred autoclave was charged with hydridocarbonyl tris(triphenylphosphine)rhodium(I) (0.046 g, 0.05 mmole), triphenylphosphine (1.3 g, 5 mmoles), acetamide (5.9 g, 100 mmoles), methyl acrylate (8.6 g, 100 mmoles) and p-dioxane (20 g). The reactor was purged of air and pressured to 100 psi with CO/H$_2$ mixture (1:1 molar ratio), then heated to ca. 100°

C. The pressure was raised to 800 psi with CO/H$_2$ mixture and maintained at this pressure for 4 hours. The system was cooled to room temperature and excess gas was vented, resulting in 37.3 g of homogeneous solution. The glc and H-nmr analyses showed the presence of dimethyl 2-formyl-2-methylglutarate at 68% selectivity and 70% methyl acrylate conversion.

EXAMPLES II–VI

Examples II through VI were conducted according to the same procedure as used in Example I. These examples typify the first embodiment of the invention wherein dimethyl 2-formyl-2-methylglutarate is formed. Data is recorded in Table I. It will be noted that:

(1) The selectivity of dimethyl 2-formyl-2-methylglutarate dropped significantly from 74% to 6% in Example 4, when acetamide is omitted from the reaction mixtures. This demonstrates the importance of a suitable nitrogen-containing promoter for Michael additions.

(2) The presence of N—Pr$_3$N in Example 6 showed some effect on the formation Product I, but it was inferior to acetamide.

TABLE I (The synthesis of dimethyl 2-formyl-2-methylglutarate (I))

| Ex. | HRh(CO)PPh$_3$)$_3$ (g) | Ph$_3$P (g) | Acetamide (g) | methyl[1] acrylate (g) | Conditions[2] | Conversion % | Selectivity[4] for % (I) | Material recovered (g) |
|---|---|---|---|---|---|---|---|---|
| 2 | 0.046 | 1.3 | 5.9 | 12.9 | 120° C., 4 hrs | 60 | 75 | 42.0 |
| 3 | 0.092 | 1.3 | 5.9 | 12.9 | 110° C., 5 hrs | 64 | 74 | 39.3 |
| 4 | 0.046 | 1.3 | 0 | 12.9 | 120° C., 4 hrs | 20 | 6 | 33.9 |
| 5 | 0.046 | 0 | 0 | 8.6 | 100° C., 4 hrs | 80 | 0 | 33.1 |
| 6. | 0.046 | 1.3 | n-Pr$_3$N 5.9 | 8.6 | 100° C., 4 hrs | 41 | 46 | 34.6 |

NOTE:
[1]p-dioxane 20.0 g was used for solvent
[2]reaction pressure: 800 psi of CO/H$_2$ (1:1 molar ratio).
[3]after the reaction, a homogeneous yellow liquid was obtained in each case.
[4]Selectivity was calculated based on converted methyl acrylate, the by-products are methyl propionate and methyl α- or β-formylpropionate.

TABLES VII–XIV

Examples VII through XIV illustrate the second embodiment of the invention wherein ethyl acrylate is converted to diethyl-2-formyl-2-methyl glutarate. These experiments were conducted using the same procedure as was used in Examples I–VI.

Data is recorded in Table II.

Data in Table II demonstrates the effects of solvent and additives on the product distribution. The additives (or solvents) such as N,N-dimethyl acetamide, DMF and N-methyl pyrrolidone, are essential for high selectivity to Compound I. Furthermore, the presence of triphenylphosphine is a requisite (Example 14) for optimum effectiveness of the process.

TABLE II (Synthesis of Dialkyl 2-Formyl-2-Methyl glutarate (I))

| Ex. | HRh(CO)(PPh$_3$)$_3$ No. | Ph$_3$P (G) | Solvent & Additives | Ethyl Acrylate (G) | Conditions | Conv. | Material Recovered (G) | Yield, % (I) | (II) | (III) |
|---|---|---|---|---|---|---|---|---|---|---|
| 7 | 0.092 | 1.3 | N,N—Dimethyl acetamide 20 g | 20 | 800 psi, CO/H$_2$ 100° C., 6 Hrs. | 100% | 44 | 66% | 33% | 0% |
| 8 | 0.092 | 1.3 | DMF 20 g | 20 | 800 psi 100° C., 4 Hrs. | 100% | 43.5 | 51% | 29% | 18% |
| 9 | 0.092 | 1.3 | MEOH 20 g | 20 | 800 psi 100° C., 6 Hrs. | 100% | 42.5 | 22% | — | — |
| 10 | 0.092 | 1.3 | N—methylpyrrolidone 20 g | 20 | 800 psi 100° C., 4 Hrs. | 100% | 42.5 | 50% | 26% | 22% |
| 11 | 0.092 | 1.3 | Toluene 20 g | 20 | 800 psi 100° C., 3.5 Hrs. | — | — | 20% | — | 8% |
| 12 | 0.092 | 1.3 | TMEDA 20 g | 20 | 800 psi 100° C., 4 Hrs. | 100% | 40.6 | 3% | 87% | 8% |
| 13 | 0.092 | 1.3 | N,N—Dimethyl acetamide 10 g | 20 | 800 psi 100° C., 5.5 Hrs. | 100% | 45.6 | 31% | 21% | 0% |
| 14 | 0.092 | 0 | N—methylpyrrolidone 20 g | 20 | 800 psi 100° C., 4 Hrs. | 100% | 40.5 | 0% | 12% | 59%* |

NOTE:
Compound (I) diethyl 2-formyl-2-methyl glutarate;
Compound (II) ethyl propionate;
Compound (III) ethyl alpha-formyl-propionate
*Et$_2$NCH$_2$CH$_2$COOC$_2$H$_5$ (48%)

What is claimed is:

1. A process for the production of alkyl 2-formyl-2-methylglutarate by the reaction of alkyl acrylates with carbon monoxide and hydrogen in the presence of a catalyst comprising a rhodium-containing compound, a phosphine-containing ligand and a nitrogen-containing compound selected from the group consisting of compounds represented by the formulas RCONH$_2$, RCONR'$_2$ or R$_3$N, where R represents an alkyl group containing 1 to 10 carbon atoms or an aryl radical optionally in the presence of a solvent from the group consisting of oxygenated hydrocarbons wherein the only oxygen atoms present are in ether groups, ester groups, ketone carbonyl groups or hydroxyl groups of alcohols at a temperature of 70°–150° C. and a pressure of 500–4000 psi.

2. The process of claim 1 wherein the alkyl acrylate is methyl acrylate, the phosphine-containing ligand is triphenylphosphine and the nitrogen-containing compound is acetamide.

3. The process of claim 1 wherein the rhodium-containing catalyst is hydridorhodium tris(triphenylphosphine)rhodium(I).

4. The process of claim 2 wherein the solvent is p-dioxane.

5. A process for the production of diethyl 2-formyl-2-methyl glutarate by the reaction of ethyl acrylate with carbon monoxide and hydrogen in the presence of a catalyst comprising a rhodium-containing compound, triphenylphosphine and an additive comprising a secondary amide at a temperature of 80°–120° C. and a pressure of 500–2000 psi.

6. The process of claim 5 wherein the amide is selected from the group consisting of acetamide, N,N-dimethylacetamide and dimethylformamide.

7. A process for the production of dimethyl 2-formyl-2-methylglutarate by the reaction of methyl acrylate with carbon monoxide and hydrogen in the presence of a catalyst comprising a rhodium-containing compound, triphenylphosphine and acetamide in the presence of an oxygenated hydrocarbon solvent in which the only oxygen atoms present are in ether groups, ester groups, ketone carbonyl groups or hydroxyl groups of alcohols at a temperature of 80° C.–120° C. and a pressure of 500 psi to 2000 psi.

* * * * *

UNITED STATES PATENT AND TRADEMARK OFFICE
CERTIFICATE OF CORRECTION

PATENT NO. : 4,849,543                         Page 1 of 2
DATED      : July 18, 1989
INVENTOR(S): Jiang-Jen Lin It is certified that error appears in the above-identified patent and that said Letters Patent is hereby corrected as shown below:

Claim 1, line 1, delete "alkyl" and substitute therefor --dialkyl--.

Claim 1, line 2, after "acrylates" insert --wherein the alkyl group has 1-10 carbon atoms--.

Claim 1, line 4, delete "a".

Claim 1, line 5, delete "phosphine-containing ligand" and substitute therefor --at least three moles of triphenylphosphine per mole of rhodium-containing compound--.

Claim 1, line 9, delete "or an aryl radical".

Claim 1, line 10, after "solvent" insert --selected--.

Claim 7, line 5, delete "triphenylphosphine" and substitute therefor --at least three moles of triphenylphosphine per mole of rhodium-containing compound--.

UNITED STATES PATENT AND TRADEMARK OFFICE
CERTIFICATE OF CORRECTION

PATENT NO. : 4,849,543
DATED : July 18, 1989
INVENTOR(S) : Jiang-Jen Lin

It is certified that error appears in the above-identified patent and that said Letters Patent is hereby corrected as shown below:

Column 1, line 19, delete "step" and substitute therefor --reaction--.

Column 4, lines 45 and 48, delete "step" and substitute therefor --embodiment--.

Column 5, line 45, delete "triphosphine" and substitute there --triphenylphosphine--.

Column 7, line 65, delete "4" and substitute --IV--.

Column 8, line 1, delete "N-$Pr_3$N" and substitute therefor --n-$Pr_3$N--; and delete "6" and substitute therefor --VI--.

Signed and Sealed this

Tenth Day of July, 1990

Attest:

HARRY F. MANBECK, JR.

*Attesting Officer*  *Commissioner of Patents and Trademarks*